US008579611B2

(12) United States Patent
Lucas

(10) Patent No.: US 8,579,611 B2
(45) Date of Patent: Nov. 12, 2013

(54) LOAD RING MOUNTING OF PUMPING PLUNGER SLEEVE

(75) Inventor: Robert Lucas, Ellington, CT (US)

(73) Assignee: Stanadyne Corporation, Windsor, CT (US)

( * ) Notice: Subject to any disclaimer, the term of this patent is extended or adjusted under 35 U.S.C. 154(b) by 1156 days.

(21) Appl. No.: 12/008,184

(22) Filed: Jan. 9, 2008

(65) Prior Publication Data

US 2008/0213112 A1 Sep. 4, 2008

Related U.S. Application Data

(60) Provisional application No. 60/879,674, filed on Jan. 10, 2007.

(51) Int. Cl.
*F04B 19/00* (2006.01)
*A61M 1/00* (2006.01)

(52) U.S. Cl.
USPC .......................................... 417/470; 417/437

(58) Field of Classification Search
USPC ........... 417/470, 471, 437; 267/160, 161, 165
See application file for complete search history.

(56) References Cited

U.S. PATENT DOCUMENTS

| | | | | |
|---|---|---|---|---|
| 2,559,364 | A * | 7/1951 | Mashinter | 239/90 |
| 4,029,071 | A * | 6/1977 | Saito et al. | 123/447 |
| 4,239,460 | A * | 12/1980 | Golz | 417/251 |
| 4,272,027 | A * | 6/1981 | Seilly et al. | 239/88 |
| 4,276,000 | A * | 6/1981 | Warwicker | 417/302 |
| 5,065,988 | A * | 11/1991 | Wedell | 267/149 |
| 5,775,203 | A | 7/1998 | Osborn et al. | 92/128 |
| 6,379,132 | B1 * | 4/2002 | Williams | 417/470 |
| 6,502,826 | B1 | 1/2003 | Schroeder et al. | |
| 7,114,928 | B2 * | 10/2006 | Asayama et al. | 417/470 |
| 2003/0056765 | A1 | 3/2003 | Onishi et al. | 123/495 |
| 2003/0161746 | A1 * | 8/2003 | Asayama et al. | 417/470 |
| 2004/0052652 | A1 | 3/2004 | Yamada et al. | 417/273 |

FOREIGN PATENT DOCUMENTS

WO WO 03/064885 A1 8/2003

OTHER PUBLICATIONS

International Search Report, PCT/US2008/000324, dated Jun. 5, 2008.

* cited by examiner

*Primary Examiner* — Charles Freay
*Assistant Examiner* — Alexander Comley
(74) *Attorney, Agent, or Firm* — Alix, Yale & Ristas, LLP

(57) ABSTRACT

A clamping and seal loading technique for securing the plunger sleeve to the pump housing of a single plunger fuel pump. This is achieved by providing a load ring between a sleeve retainer and the sleeve, such that the axial force applied by the retainer during installation and attachment to the plunger bore wall of the housing, is distributed more evenly on the sleeve and the sealing surface of the sleeve against the housing adjacent to the pumping chamber. The even distribution of force minimizes misalignment of the sleeve and thus maintains concentricity between the sleeve and the plunger.

20 Claims, 4 Drawing Sheets

LOAD RING MOUNTING OF PUMPING PLUNGER SLEEVE

RELATED APPLICATION

This application claims priority under 35 U.S.C. 119(e) from U.S. Provisional Application No. 60/879,674 filed Jan. 10, 2007 for "Load Ring Mounting of Pumping Plunger", the entire disclosure of which is hereby incorporated by reference.

BACKGROUND

The present disclosure relates generally to fuel pumps, and is more particularly concerned with a new and improved single plunger fuel pump.

In a typical high pressure, reciprocating plunger fuel supply pump, the plunger reciprocates within a surrounding sleeve which is secured in the plunger bore hole. The sleeve bears on a shoulder or other mounting surface in the housing. To achieve ideal performance and long life, the plunger OD and the sleeve ID must be precisely sized with close tolerances and installed in a manner that preserves a precise fit.

Notwithstanding the precision with which the sleeve and plunger may be fabricated, the installation in the pump housing can produce slight misalignment of the plunger within the sleeve. This misalignment can cause excessive or non-uniform wear on the plunger, and can also affect the fluid seal between the sleeve and the housing, giving rise to excessive leakage. Such misalignment is due to an imbalance or asymmetry in the axial force applied around on the sleeve to bear against the mounting surface of the housing.

SUMMARY

It is an object to provide an improved clamping and seal loading technique for securing the plunger sleeve to the pump housing of a single plunger fuel pump.

This object is achieved by providing a load ring between a sleeve retainer and the sleeve, such that the axial force applied by the retainer during installation is distributed more evenly on the sleeve and the mounting surface of the housing.

In a preferred embodiment, the invention is directed to a single plunger fuel pump comprising a housing having an internal pumping chamber and an inlet valve that feeds the pumping chamber, a plunger assembly mounting bore in the housing defining a bore wall and an end wall having an opening in fluid communication with the pumping chamber, and a plunger sleeve in the plunger assembly mounting bore adjacent the pumping chamber. The plunger sleeve has a seal face at one end which bears on and seals against a seal surface at the end wall of the mounting bore. A pumping plunger is reciprocable in the plunger sleeve inwardly toward and outwardly away from the pumping chamber. A plunger sleeve retainer is secured against the mounting bore wall and axially supports the sleeve. A plunger return spring is captured between a spring seat at the outer end of the plunger and a shoulder on the sleeve retainer. A load ring is situated between the sleeve retainer and the sleeve, urging the sleeve inwardly with sufficient force to maintain concentricity of the plunger within the sleeve and sealingly press the sealing face of the sleeve against the sealing surface at the end wall of the bore.

In an alternative form, the invention is directed a plunger assembly for a fuel pump comprising, a plunger sleeve having upper and lower ends, a substantially tubular body defining a pumping axis, and a radially extending external shoulder. A substantially tubular sleeve retainer concentrically receives the body of the sleeve, with a first radially extending external shoulder facing the shoulder on the sleeve. A pumping plunger is concentrically disposed in the plunger sleeve and retainer, with an upper end adjacent the upper end of the sleeve and a lower end projecting from the retainer. A plunger return spring is captured between a spring seat at the lower end of the plunger and a second shoulder on the sleeve retainer. A load ring is situated between the sleeve retainer first shoulder and the sleeve shoulder.

Preferably, the sleeve floats on the load ring until the sleeve retainer is advanced and secured within the bore a sufficient distance to form a seal between the seal face at one end which bears on and seals against a seal surface at the end wall of the mounting bore. The load ring is situated between the inner end of the sleeve retainer and a shoulder on the sleeve, urging the sleeve inwardly with a substantially constant force to sealingly press the sealing face of the sleeve against the sealing surface at the end wall of the bore.

Whether the retainer is advanced against the sleeve by threaded engagement or interference fit, the sleeve is uniformly urged by the retainer against the housing mounting surface, thereby maintaining alignment of the plunger within the sleeve and integrity of the seal between the sleeve and the housing.

BRIEF DESCRIPTION OF THE DRAWING

In the accompanying drawing, like elements are numbered alike in the several Figures.

DETAILED DESCRIPTION

Figure 1:
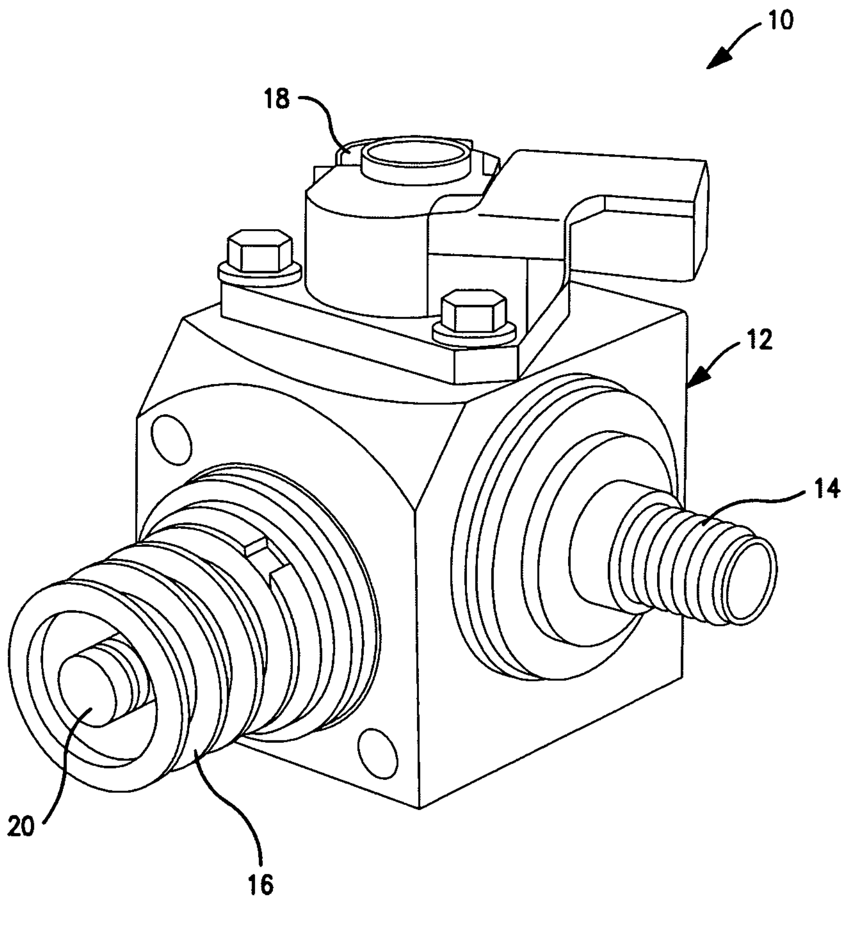
FIG. 1 is a perspective view of a one plunger fuel pump having a substantially cubic housing or body, with the fuel inlet connector projecting on the right, the single plunger actuation assembly projecting from the left, and the inlet control valve projecting from the top.

FIG. 1 shows a one plunger fuel pump 10 having a substantially cubic housing or body 12, with the fuel inlet connector 14 projecting from the right, the single plunger actuation assembly 16 projecting from the left, and the inlet control valve 18 projecting from the top.

Figure 2:
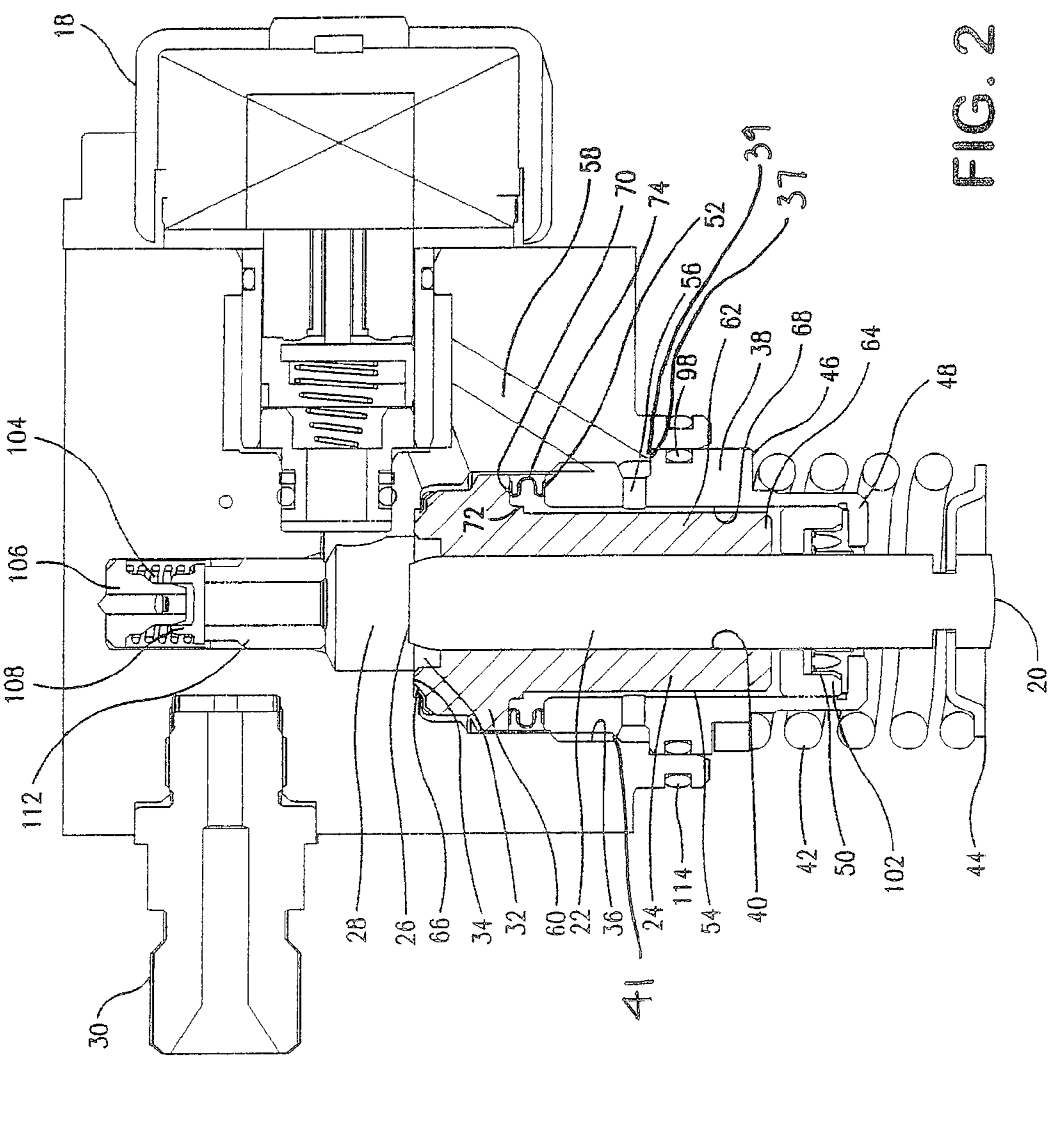
FIG. 2 is a staggered section view of the pump of FIG. 1, through the inlet control valve, pumping plunger, and outlet connection, showing one embodiment of the improved clamping and seal loading technique for securing the plunger sleeve to the pump housing.

With reference now to FIGS. 1 and 2, it is readily understood that the engine drive shaft carries a lobed cam (not shown) that reciprocates the remote end 20 of the pumping plunger 22 within a pumping sleeve 24 secured to the housing, between fuel charging (intake) and discharging (output) phases. The other, pumping end 26 of the plunger is situated in the pumping chamber 28, which fills with fuel at a feed pressure of up to about 4 bar during the charging phase and, preferably subject to initial spill control, pressurizes the fuel in the pumping chamber up to about 200 bar for delivery via a discharge fitting 30 to, e.g., the common rail (not shown). The fuel is fed directly to the pumping chamber 28 through a solenoid controlled inlet valve 18. As used herein, “inner” and “outer” refer to directions toward and away from the pumping chamber, respectively.

The substantially cylindrical pumping plunger 22 is carried concentrically in the plunger sleeve 24, which at one end 32 bears on or is otherwise sealed against the end wall 34 of the plunger assembly mounting bore 36 in the housing, and which must be laterally fixed directly or indirectly to the mounting bore. A plunger sleeve retainer 38 is press fit or threaded against the mounting bore wall 40 for this purpose. The plunger 22 is disposed concentrically in the inner wall 40 of the sleeve 24 and the retainer 38. A plunger return spring 42 is captured between a spring seat 44 at the driven end 20 of the plunger and a shoulder 46 on the sleeve retainer. The outer end 48 of the plunger sleeve retainer is turned inward to capture a lip seal 50 for sealing fuel within the pump. The upper end of the retainer forms a shoulder 52.

Any leakage around the inner end 32 of the plunger sleeve 24 enters the clearance 54 with the ID of the tubular body of sleeve retainer 38 and is directed back to the lower pressure at the inlet valve 18, via leak off ports 56 in the retainer and an internal passage 58 through the housing.

Figure 3A:
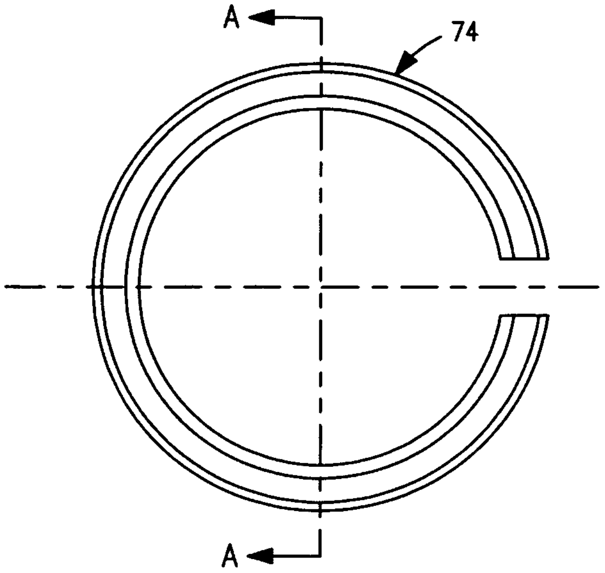
FIGS. 3A and 3B are enlarged detailed views of the load ring shown in FIG. 2, with FIG. 3B taken along section line A-A of FIG. 3A.
Figure 3B:
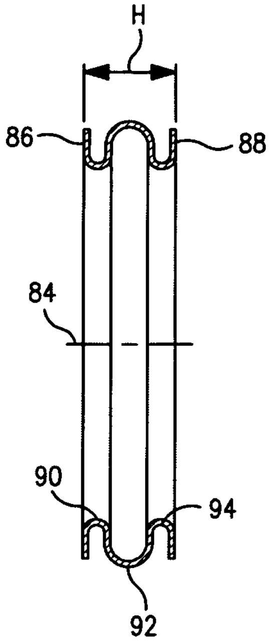

In the embodiment of FIGS. 1-3, the sleeve 24 has an enlarged inner end portion 60 adjacent the pumping chamber 28 and a tubular body portion 62 extending to an outer end 64. The inner end has a sealing rim or bead 66 that is urged against the sealing surface at the end wall 34 of the bore in the housing that receives the sleeve retainer and sleeve. This sealing surface surrounds the plunger near the pumping chamber and when properly sealed prevents pumped fuel from leaking along the outer surface of the sleeve and sleeve retainer. The body 62 of the sleeve is situated within the cylindrical inner wall 68 of the sleeve retainer, whereas the enlarged portion 60 at the inner end of the sleeve is formed with an integral flange or otherwise defines a downward facing shoulder 70 that axially registers with and is spaced 72 from the inner end 52 of the retainer.

A load ring 74 is situated between the inner end 52 of the retainer and the shoulder 70 on the sleeve. The sleeve 24 floats on the load ring 74 until the retainer 38 is advanced within the housing bore 36 a sufficient distance to press the sealing rim or bead 66 of the sleeve against the sealing surface 34 at the end wall of the bore. When this condition is reached during assembly, the retainer is fixed with respect to the bore, as by retainer external shoulder 39 bottoming out as a hard stop against the shoulder 37 on the housing, thereby preventing further inward axial movement. This can be achieved with a threaded connection 41 between the retainer and the bore, or the retainer can be press (interference) fit. The shape of the load ring affords considerable tolerance on the effective positioning of the retainer within the bore. The reason for the load ring as opposed to traditional threaded clamping or press-fit designs is to reduce the sleeve ID distortion at the critical interface with the plunger OD. The load ring applies a very consistent, predictable load.

Figure 4:
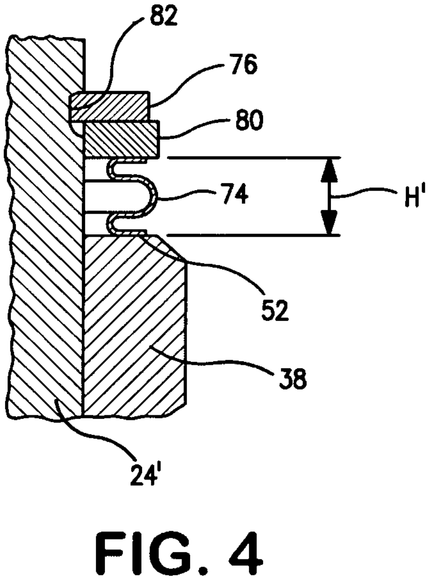
FIG. 4 is an enlarged view of an alternative embodiment of the improved clamping and seal loading technique for securing the plunger sleeve to the pump housing.

FIG. 3 shows the preferred load ring 74, and FIG. 4 shows such ring in an alternative to the integral shoulder flange 70, which would typically have a machined face for interacting with the load ring. According to the embodiment of FIG. 4, the machined face is replaced with a snap ring 76 and washer 80. The sleeve 24' has a circumferential groove 82 to receive and retain the snap ring. With the latter embodiment, less material is required to fabricate the sleeve.

The load ring 74 is preferably a split or C-shaped ring having a cross section (taken parallel to the axis 84) that generally resembles the letter “W”. The load ring can, however, be a full ring. Preferably, each outer leg 86, 88 (at the axial ends) is substantially perpendicular to the axis 84 with all the corners 90, 92, 94 contoured rather than sharp. The legs are spaced apart a free height H when the ring is not loaded, but move toward each other during loading by the sleeve retainer 38, to a shorter, compressed height H'. In a typical application, the load ring can be 20-25 mm across the greatest diameter (at 92), and 4 to 5 mm less across the smallest diameter (at 90, 94), for axially transmitting a target seal load of 750-1500 lbs. across a surface area defined by the legs, in the range of 0.0001 to 0.0002 $m^2$. As a representative but not limiting example, the free height H of the load ring can be about 4.0 mm, whereas the compressed height H' for transmitting the target load can range between about 2.0 to 3.0 mm (i.e., a compression of about 1-2 mm).

As noted above with reference to FIG. 2, any leakage past the seal at 66 is at a low pressure and passes through ports 56 in the retainer 38 into the passage 58 leading to a low pressure volume such as at the inlet valve. Any other potential leakage is blocked by an O-ring 98 or the like situated between an enlarged diameter portion of the retainer outside the leak off port 56, and a similarly enlarged portion of the housing bore.

Figure 5:
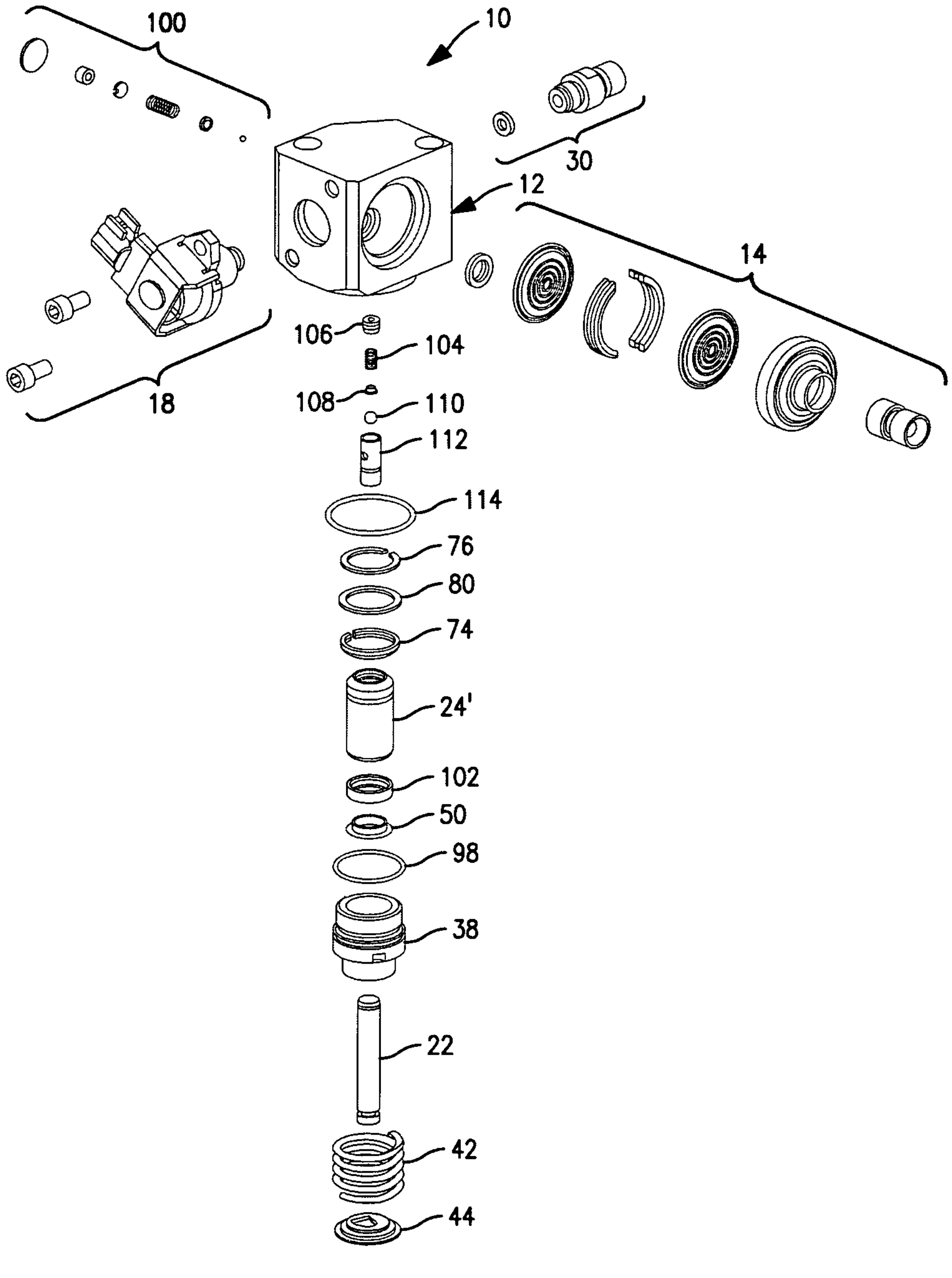
FIG. 5 is an exploded view of the pump of FIG. 1, with the embodiment of FIG. 4.

FIG. 5 is an exploded view of the embodiment of FIG. 4, with like structure indicated by like numerals. The inlet fitting assembly 14 forms no part of the present invention, but preferably has a bellows type inlet pressure attenuator such as described in the priority patent application. The inlet valve assembly 18 may be of any conventional type, preferably solenoid controlled. Additionally to the structure previously described with respect to FIGS. 1-4, FIG. 5 shows an overpressure check valve assembly 100. The lip seal 50 at the outer end of the plunger is shown separated from its retainer 102. It is well within the ordinary skill in the art to select an appropriate check valve assembly between the pumping chamber 28 and the discharge fitting 30. In the version shown in FIGS. 2 and 5, a spring 104 has a cap 106 and a seat 108, aligned with ball 110 and another seat 112. Also shown is another O-ring 114 for placement in a groove on the neck of the housing, where the housing is mounted to the engine.

While preferred embodiments have been set forth for purposes of illustration, the foregoing description should not be deemed a limitation of the disclosure herein. Accordingly, various modifications, adaptations and alternatives may occur to one skilled in the art without departing from the spirit and scope of the present disclosure.

What is claimed:

1. A single plunger fuel pump comprising:

a pump housing having an internal pumping chamber and a pressurized inlet line to an inlet valve that feeds the pumping chamber;

a plunger assembly mounting bore in the housing defining a bore wall, a bore axis, and an end wall having an opening in fluid communication with the pumping chamber;

a plunger sleeve in the plunger assembly mounting bore adjacent the pumping chamber, said plunger sleeve having a seal face at one end which bears on and seals against a seal surface at the end wall of the mounting bore;

a pumping plunger reciprocable in the plunger sleeve inwardly toward and outwardly away from the pumping chamber;

a plunger sleeve retainer secured at a predetermined position against the mounting bore wall and axially supporting the sleeve;

a plunger return spring captured between a spring seat at an outer end of the plunger and a shoulder on the sleeve retainer; and a load ring situated between the sleeve retainer and the sleeve, urging the sleeve inwardly with a predetermined force determined by said position of the sleeve retainer sufficient to sealingly press the seal face of the sleeve against the seal surface at the end wall of the bore.

2. The pump of claim 1, wherein the load ring has a cross section taken parallel to the bore axis that generally resembles the letter “W” with a plurality of adjacent legs that meet at an apex.

3. The pump of claim 2, wherein the load ring has outer legs and each outer leg of the load ring is substantially perpendicular to the bore axis with the apex rounded.

4. The pump of claim 1, wherein the sleeve floats on the load ring until the sleeve retainer is advanced and secured within the bore against a predetermined stop within the bore and thereby forms a seal between the seal face at one end which bears on and seals against said seal surface at the end wall of the mounting bore with said predetermined force.

5. The pump of claim 1, wherein the load ring is situated between the inner end of the sleeve retainer and a shoulder on the sleeve, urging the sleeve inwardly with a substantially constant force to sealingly press the seal face of the sleeve against the seal surface at the end wall of the bore.

6. The pump of claim 1, wherein the sleeve retainer is threaded to the plunger assembly mounting bore.

7. The pump of claim 1, wherein the sleeve retainer is press fit to the plunger assembly mounting bore.

8. The pump of claim 1, wherein the sleeve is substantially tubular with inner and outer ends, the retainer is substantially tubular with inner and outer ends, and the outer end of the sleeve is situated coaxially within the retainer closer to the outer end of the retainer than to the inner end of the retainer.

9. The pump of claim 1, wherein the sleeve carries a snap ring at least in part forming said shoulder on the sleeve, spaced inwardly from the inner end of the retainer, and the load ring is interposed between the snap ring and a shoulder on the retainer.

10. The pump of claim 9, wherein the shoulder on the sleeve includes a washer between the snap ring and the load ring is compressed between the washer and the retainer shoulder.

11. The pump of claim 1, wherein the load ring is resilient between a free height and a final compression of about 1-2 mm under an installation load of 750-1500 lbs.

12. The pump of claim 11, wherein the load ring has a free height of about 4.0 mm, and the compressed height is between about 2.0 to 3.0 mm.

13. The pump of claim 1, wherein a radial clearance is formed between the sleeve and the retainer;

the retainer has a leak off port located outwardly of the load ring and having a radially inner end in fluid communication with the clearance; and the leak off port has a radially outer end in fluid communication with a low pressure region of the pump.

14. A single plunger fuel pump comprising:

a pump housing having an internal pumping chamber and an inlet line to an inlet valve that feeds the pumping chamber;

a plunger assembly mounting bore in the housing defining a bore wall and an end wall having an opening in fluid communication with the pumping chamber;

a plunger sleeve in the plunger assembly mounting bore adjacent the pumping chamber, said plunger sleeve having a seal face at one end which bears on and seals against a seal surface at the end wall of the mounting bore;

a pumping plunger reciprocable in the plunger sleeve inwardly toward and outwardly away from the pumping chamber;

a plunger sleeve retainer secured against the mounting bore wall and axially supporting the sleeve;

a plunger return spring captured between a spring seat at an outer end of the plunger and a shoulder on the sleeve retainer; and a partially compressible load ring situated between the sleeve retainer and the sleeve, urging the sleeve inwardly with sufficient force to sealingly press the seal face of the sleeve against the seal surface at the end wall of the bore; wherein the sleeve is substantially tubular with inner and outer ends, the retainer is substantially tubular with inner and outer ends, and the outer end of the sleeve is situated coaxially within the retainer closer to the outer end of the retainer than to the inner end of the retainer, the load ring is situated between the inner end of the sleeve retainer and a shoulder on the sleeve, and the sleeve floats on the load ring until the sleeve retainer is advanced and secured within the bore against a hard stop within the bore to compress the load ring a predetermined amount thereby urging the sleeve inwardly with a substantially constant predetermined force against the end wall of the bore and concentrically aligning the sleeve with the plunger.

15. The pump of claim 14, wherein the sleeve carries a snap ring at least in part forming said shoulder on the sleeve, spaced inwardly from the inner end of the retainer, and the load ring is interposed between the snap ring and a shoulder on the retainer;

the shoulder on the sleeve includes a washer between the snap ring and the load ring, and the load ring is compressed between the washer and the retainer shoulder; and the load ring is resilient between a free height and final installed compression under an installation load of 750-1500 lbs.

16. A plunger assembly for mounting in a housing of a fuel pump comprising:

a plunger sleeve having upper and lower ends, a substantially tubular body defining a pumping axis, and a radially extending external shoulder;

a substantially tubular sleeve retainer in which the body of the sleeve is coaxially received, with a first radially extending external shoulder facing the shoulder on the sleeve;

a pumping plunger coaxially disposed in the plunger sleeve and retainer, with an upper end adjacent the upper end of the sleeve and a lower end projecting from the retainer;

a plunger return spring captured between a spring seat at the lower end of the plunger and a second shoulder on the sleeve retainer;

a third external shoulder on the sleeve retainer, situated axially between the first and second shoulders for abutting a hard stop in the housing; and a load ring situated between the sleeve retainer first shoulder and the sleeve shoulder, urging the sleeve upward relative to the sleeve retainer with a substantially constant predetermined force when the third external shoulder abuts said hard stop.

17. The plunger assembly of claim 16, wherein the load ring has a cross section taken parallel to the ring axis that generally resembles the letter “W” with a plurality of adjacent legs that meet at an apex.

18. The plunger assembly of claim 17, wherein the load ring has outer legs and each outer leg is substantially perpendicular to the axis with the apex rounded.

19. The plunger assembly of claim 16, wherein the load ring has a face area against the sleeve shoulder in the range of 0.0001 to 0.0002 $m^2$ and is resilient between a free height and final compression under an installation load of 750-1500 lbs.

20. The pump of claim 4, wherein the sleeve retainer has an external shoulder that abuts a shoulder stop in the bore wall when the sleeve retainer is fully advanced and fixed within the bore.

* * * * *